US00PP19594P2

(12) United States Plant Patent
Zaiger et al.

(10) Patent No.: US PP19,594 P2
(45) Date of Patent: Dec. 23, 2008

(54) PEACH TREE NAMED 'SWEET JUANA'

(50) Latin Name: *Prunus persia*
Varietal Denomination: Sweet Juana

(76) Inventors: Gary Neil Zaiger, 1907 Elm Ave., Modesto, CA (US) 95358; Leith Marie Gardner, 1207 Grimes Ave., Modesto, CA (US) 95358; Grant Gene Zaiger, 4005 California Ave., Modesto, CA (US) 95358

( * ) Notice: Subject to any disclaimer, the term of this patent is extended or adjusted under 35 U.S.C. 154(b) by 0 days.

(21) Appl. No.: 12/012,466

(22) Filed: Feb. 4, 2008

(51) Int. Cl.
*A01H 5/00* (2006.01)

(52) U.S. Cl. ..... Plt./197
(58) Field of Classification Search ..... Plt./197
See application file for complete search history.

*Primary Examiner*—Annette H Para

(57) ABSTRACT

A new and distinct variety of peach tree (*Prunus persica*). The following features of the tree and its fruit are characterized with the tree budded on 'Nemagaurd' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. The tree being a regular and productive bearer of large size fruit.
2. Fruit holding firm on the tree 7 to 8 days after maturity (shipping ripe).
3. Producing fruit with a high degree of attractive red skin color.
4. Vigorous, upright tree growth.
5. Fruit with a mild, sweet, sub-acid flavor.
6. Fruit with good storage and handling quality.

1 Drawing Sheet

Botanical classification: *Prunus persica.*

BACKGROUND OF THE VARIETY:

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of peach tree was originated and asexually reproduced by us in our experimental orchard located near Modesto, Stanislaus County, Calif.

PRIOR VARIETIES:

Among the existing varieties of peaches and nectarines, which are known to us, and mentioned herein, 'Zee Lady' Peach (U.S. Plant Pat. No. 5,832), 'O'Henry' Peach (U.S. Plant Pat. No. 2,964) and 'Giant Babcock' Peach (U.S. Plant Pat. No. 1,353), 'Summer Sweet' Peach (U.S. Plant Pat. No. 8,07O) and 'May Grand' Nectarine (U.S. Plant Pat. No. 2,794).

ORIGIN OF THE VARIETY:

The new and distinct variety of peach tree (*Prunus persica*) was developed by us in our experimental orchard located near Modesto, Calif. from seed of an open pollinated proprietary seedling with the field identification number '378LN103', (the pollen parent is unknown). The seed parent '378LN103' originated from multiple crosses of the following peaches and nectarines, 'O'Henry' (U.S. Plant Pat. No, 2,964), 'Summer Sweet' (U.S. Plant Pat. No. 8,070), 'Giant Babcock' (U.S. Plant Pat. No. 1,353), 'Zee Lady'

(U.S. Plant Pat. No. 5,832) and 'May Grand' (U.S. Plant Pat. No. 2,794) with various proprietary selected peach seedlings. A large number of these open pollinated seedlings were planted and grown on their own root system. Under close and careful observation, one such seedling, which is the present variety, exhibited desirable tree and fruit characteristics and in 2002, was selected for asexual propagation and commercialization.

ASEXUAL REPRODUCTION OF THE VARIETY:

Asexual reproduction of the new and distinct variety of peach tree was by budding to 'Nemagaurd' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY:

The present new variety of peach tree (*Prunus persica*) is of large size, vigorous, upright growth and a productive and regular bearer of large size, late maturing, yellow flesh, clingstone fruit that is mild sweet, sub-acid, with very good flavor and eating quality. The fruit is further characterized by having an attractive red skin color, holding firm on the tree 7–8 days after maturity (shipping ripe) and being relatively uniform in size throughout the tree. In comparison to the proprietary seed parent '378LN103', the fruit of the new variety has yellow flesh, compared to white flesh, is larger in size and is approximately one week later in maturity. In comparison to the 'O'Henry' Peach (U.S. Plant Pat. No. 2,964), the fruit of the new variety is sub-acid in flavor compared to acidic, is similar in size and approximately 2 weeks later in maturity.

PHOTOGRAPH OF THE VARIETY:

The accompanying color photographic illustration shows typical specimens of the foliage and fruit of the present new peach variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY:

The following is a detailed botanical description of the new variety of peach tree, its flowers, foliage and fruit, as based on observations of 6 year old specimens grown near Modesto, Calif., with color in accordance with Munsell Book of Color.

TREE:

*Size.*—Large, normal for most standard commercial peach varieties. Pruned to 3 to 3.5 meters in height for economical harvesting of fruit. Average spread 3 meters, varies with cultural practices.

*Form.*—Upright, usually pruned to vase shape.

*Vigor.*—Vigorous, growth of 1.5 to 2 meters in height the first growing season. Varies with type and fertility of soil and climatic conditions.

*Branching habit.*—Upright, crotch angle approximately 35°, increases with heavy crop load.

*Productivity.*—Productive, fruit thinning and spacing necessary for desired market size.

*Bearer.*—Regular, adequate fruit set 4 consecutive years, no alternate bearing observed.

*Fertility.*—Self fertile.

*Density.*—Medium dense, usually pruned to vase shape, which allows more sunlight to center of tree to enhance fruit color and health of fruit wood.

*Hardiness.*—Hardy in all fruit growing areas of California. Tree grown in USDA Hardiness Zone 9. Winter chilling requirement approximately 900 hours at or below 45° F.

Trunk:

*Size.*—Large. Average circumference 58.4 cm at 25.4 cm above ground on a 6 year old tree.

*Stocky.*—Medium stocky.

*Texture.*—Medium shaggy, roughness increases with age.

*Color.*—Varies from 7.5YR 3/2 to 10YR 4/2.

BRANCHES

*Size.*—Medium size. Average circumference 19.0 cm at 1.2 meters above ground. Crotch angle approximately 35°, increases with crop load.

*Surface texture.*—New growth relatively smooth. Mature growth medium rough, roughness increases with age.

*Lenticels.*—Size — large. Average number 37 in a 25.8 square cm area. Average length 4.1 mm. Average width 1.9 mm. Color varies from 7.5YR 6/8 to 7.5YR 5/8.

*Color.*—New growth varies from 2.5GY 6/8 to 2.5GY 5/8. Mature growth varies from 7.5YR 4/2 to 10YR 3/4, varies with age of growth.

Leaves

*Size.*—Large. Average length 156.0 mm. Average width 41.1 mm.

*Form.*—Lanceolate.

*Apex.*—Acuminate.

*Base.*—Cuneate.

*Margin.*—Crenate.

*Thickness.*—Medium.

*Surface texture.*—Upper surface relatively smooth, slightly indented over midrib and leaf veins, glabrous. Lower surface relatively smooth with small ridges created by midrib and pinnate venation, glabrous.

*Petiole.*—Average length 9.7 mm. Average width 1.6 mm. Grooved longitudinally. Surface glabrous. Color varies from 5GY 7/6 to 5GY 6/4.

*Glands.*—Type — reniform. Size — medium. Average length 1.2 mm. Average diameter 0.9 mm. Number — average 4, varies from 3 to 6. Location — primarily located on base of leaf blade and upper portion of petiole. Color varies from 2.5GY 5/8 to 5GY 5/6.

*Color.*—Upper surface varies from 5GY 3/4 to 5GY 3/6. Lower surface varies from 5GY 5/4 to 5GY 4/4. Midvein color varies from 2.5GY 8/6 to 5GY 7/6.

Flower buds:

*Size.*—Medium to large. Average length 13.7 mm. Average diameter 8.2 mm.

*Hardiness.*—Hardy with respect to California winters.

*Form.*—Conical, becoming elongated before opening.

*Pedicel.*—Average length 3.1 mm. Average width 1.5 mm. Color varies from 5GY 6/6 to 5GY 5/8.

*Color.*—Varies from 7.5RP 8/6 to 7.5RP 6/10.

Flowers

*Blooming period.*—Date of First Bloom Mar. 2, 2007. Date of Petal Fall Mar. 13, 2007, varies slightly with climatic conditions.

*Size.*—Large, showy. Average height 19.9 mm. Average diameter 38.5 mm.

*Petals.*—Number —5, alternately arranged to sepals. Size — large. Average length 18.5 mm. Average width 17.9 mm. Form — orbicular, narrows slightly at point of attachment. Margin — sinuate. Color — varies from 5RP 8/4 to 7.5RP 8/4. Both upper and lower surfaces glabrous.

*Sepals.*—Number —5, alternately arranged to petals; Size — medium. Average length 5.9 mm. Average width 5.0 mm. Shape — triangular, apex rounded. Margin — entire. Surface — upper surface glabrous, lower surface pubescent. Color — upper surface varies from 5GY 5/6 to 2.5R 4/10. Lower surface varies from 2.5R 3/4 to 2.5R 3/6.

*Stamens.*—Average number per flower 44. Average filament length 15.0 mm. Filament color varies from N 9.5/ (white) to 5RP 7/6. Anther color varies from 5R 3/8 to 5R 3/10.

*Pollen.*—Self fertile. Color varies from 5Y 8/10 to 5Y 7/10.

*Pistil.*—Number — normally one. Surface — pubescent. Average length 14.6 mm. Position of stigma average 1.4 mm below anthers. Color varies from 10Y 8.5/6 to 2.5GY 6/8.

*Fragrance.*—Moderate aroma.

*Color.*—Varies from 5RP 8/6 to 7.5RP 8/4.

*Number flowers per flower buds.*—One.

*Pedicel.*—Average length 3.3 mm. Average width 1.8 mm. Color varies from 2.5GY 6/6 to 5GY 6/6.

Fruit:

*Maturity when described.*—Firm ripe.

*Date of first picking.*—Aug. 20, 2007.

*Date of last picking.*—Aug. 29, 2007, varies slightly with climatic conditions.

*Size.*—Large. Average diameter axially 64.3 mm. Average transversely in suture plane 78.7 mm. Average weight 235.7 grams, varies slightly with fertility of the soil, amount of thinning and climatic conditions.

*Form.*—Globose.

*suture.*—Nearly smooth, extends from base to apex.

*Ventral surface.*—Relatively smooth, some fruit slightly lipped.

*Apex.*—Varies from rounded to slight tip.

*Base.*—Varies from flat to slightly retuse.

*Cavity.*—Rounded to slightly elongated in suture plane. Average depth 4.6 mm. Average diameter 12.0 mm.

Stem:

*Size.*—Small to medium. Average length 7.5 mm. Average diameter 2.9 mm.

*Color.*—Varies from 10Y 6/6 to 2.5GY 7/8.

Flesh

*Ripens.*—Evenly.

*Texture.*—Firm, meaty.

*Fibers.*—Few, small, tender.

*Firmness.*—Good, comparable to the commercial peach variety 'O'Henry' (U.S. Plant Pat. No. 2,964).

*Aroma.*—Moderate.

*Amydgalin.*—Undetected.

*Eating quality.*—Very good.

*Flavor.*—Very good, mild, sweet, sub-acid.

*Juice.*—Moderate, enhances flavor.

*Brix.*—Average 14.5°, varies slightly with amount of fruit per tree and climatic conditions.

*Color.*—Varies from 10YR 8/8 to 10YR 8/10. Pit cavity varies from 5R 3/4 to 7.5R 2/6, bleeding into flesh.

Skin:

*Thickness.*—Medium.

*Surface.*—Smooth.

*Pubescence.*—Moderate amount, very short.

*Tendency to crack.*—None.

*Color.*—Ground color varies from 2.5Y 8.5/6 to 2.5Y 8.5/8, overspread with 7.5R 4/12 to 7.5R 5/6.

*Tenacity.*—Tenacious to flesh.

*Astringency.*—Undetected.

Stone:

*Type.*—Clingstone.

*Size.*—Large. Average length 31.5 mm. Average width 23.5 mm. Average thickness 19.8 mm.

*Form.*—Ovoid.

*Base.*—Varies from round to flat.

*Apex.*—Pointed. Average length 2.9 mm.

*Surface.*—Pitted throughout, pits vary from round to elongated.

*Sides.*—Unequal, one side extending further from suture plane.

*Ridges.*—Relatively smooth, wide, extending from base to apex.

*Tendency to split.*—None.

*Color.*—Varies from 7.5R 2/4 to 10R 3/4.

Kernel:

*Size.*—Medium to large. Average length 16.0 mm. Average width 11.3 mm. Average depth 6.7 mm.

*Shape.*—Ovoid.

*Viability.*—Viable.

*Skin.*—Color varies from 5Y 8.5/6 to 5Y 8/8.

Use: Dessert. Market — local and long distance.

Keeping quality: Good, held firm in cold storage at 38° to 42° F. for 3 weeks without internal breakdown or appreciable loss of flavor.

Shipping quality: Good, minimal skin scarring or bruising of flesh during picking, packing and shipping trials.

Plant/fruit disease resistance/susceptibility: No specific testing for relative plant/fruit disease resistance/susceptibility has been designed. Under close observation during planting, growing, and harvesting of fruit, under normal cultural and growing conditions near Modesto, Calif., no particular plant/fruit disease resistance or susceptibility has been observed. Any variety or selection observed during indexing of plant characteristics with abnormal fungus, bacterial, virus or insect susceptibility is destroyed and eliminated from our breeding program.

The present new variety of peach tree, its flowers, foliage and fruit herein described may vary in slight detail due to climate, soil conditions and cultural practices under which the variety may be grown. The present description is that of the variety grown under the ecological conditions prevailing near Modesto, Calif.

What is claimed is:

1. The present new variety of peach tree (*Prunus persica*), substantially as illustrated and described, characterized by its large size, vigorous, upright growth, being a productive and regular bearer of large size, late maturing, yellow flesh, clingstone fruit with a very good flavor and eating quality; the fruit is further characterized by having an attractive red skin color and being relatively uniform in size throughout the tree.

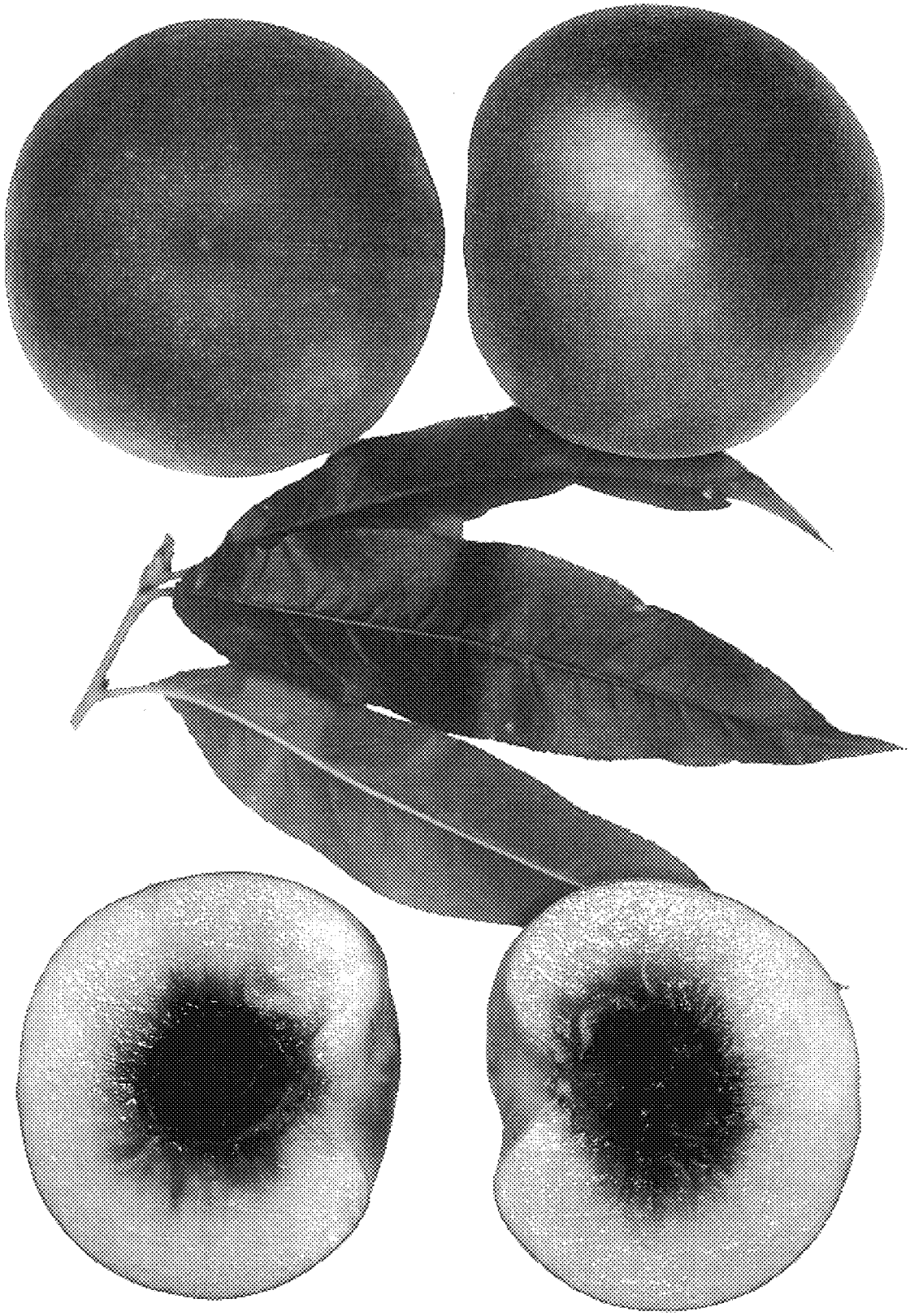

* * * * *